(12) United States Patent
Suzuki et al.

(10) Patent No.: US 10,588,488 B2
(45) Date of Patent: Mar. 17, 2020

(54) CONTROLLER AND INSERTION APPARATUS

(71) Applicant: OLYMPUS CORPORATION, Tokyo (JP)

(72) Inventors: Takashi Suzuki, Hino (JP); Fumiyuki Onoda, Tama (JP); Keijiro Omoto, Hachioji (JP); Takashi Yamashita, Hachioji (JP); Yasuaki Natori, Akishima (JP); Yoshitaka Umemoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/123,070

(22) Filed: Sep. 6, 2018

(65) Prior Publication Data

US 2019/0000303 A1 Jan. 3, 2019

Related U.S. Application Data

(63) Continuation of application No. PCT/JP2017/015438, filed on Apr. 17, 2017.

(30) Foreign Application Priority Data

Apr. 18, 2016 (JP) ................................ 2016-083014

(51) Int. Cl.
*A61B 1/00* (2006.01)
*A61B 1/07* (2006.01)
(Continued)

(52) U.S. Cl.
CPC ...... *A61B 1/00057* (2013.01); *A61B 1/00006* (2013.01); *A61B 1/00059* (2013.01);
(Continued)

(58) Field of Classification Search
CPC ............ A61B 1/00006; A61B 1/00156; A61B 1/00057; A61B 1/00059; A61B 1/00133;
(Continued)

(56) References Cited

U.S. PATENT DOCUMENTS

| 7,018,331 B2 * | 3/2006 | Chang ................ A61B 1/00059 600/118 |
| 2012/0302831 A1 | 11/2012 | Ashida et al. |
| 2013/0158349 A1 * | 6/2013 | Ashida ................ A61B 1/00059 600/109 |

FOREIGN PATENT DOCUMENTS

| JP | 2007-307241 A | 11/2007 |
| JP | 2012-245052 A | 12/2012 |

(Continued)

OTHER PUBLICATIONS

English translation of International Preliminary Report on Patentability dated Nov. 1, 2018, together with the Written Opinion received in related International Application No. PCT/JP2017/015438.

(Continued)

*Primary Examiner* — Aaron B Fairchild
(74) *Attorney, Agent, or Firm* — Scully, Scott, Murphy & Presser, P.C.

(57) ABSTRACT

A controller which controls an operation of a self-propelled mechanism of an endoscope includes an inspection control section, a usual control section, an endoscope connection detection circuit and a control switch section. The endoscope connection detection circuit detects that the endoscope has been connected. The control switch section determines whether or not the inspection operation is performed for the endoscope at the time of the connection of the endoscope, causes the usual control section to perform the usual operation when the inspection operation is performed, and causes the inspection control section to perform the inspection (Continued)

operation and then causes the usual control section to perform the usual operation when the inspection operation is not performed.

10 Claims, 9 Drawing Sheets

(51) Int. Cl.
| | |
|---|---|
| *A61B 1/06* | (2006.01) |
| *H04N 5/225* | (2006.01) |
| *A61B 1/005* | (2006.01) |
| *A61B 1/045* | (2006.01) |
| *A61B 1/05* | (2006.01) |
| *G02B 23/24* | (2006.01) |

(52) U.S. Cl.
CPC ........ *A61B 1/00156* (2013.01); *A61B 1/0002* (2013.01); *A61B 1/00009* (2013.01); *A61B 1/00045* (2013.01); *A61B 1/0051* (2013.01); *A61B 1/045* (2013.01); *A61B 1/05* (2013.01); *A61B 1/0669* (2013.01); *A61B 1/0684* (2013.01); *A61B 1/07* (2013.01); *G02B 23/2469* (2013.01); *H04N 2005/2255* (2013.01)

(58) Field of Classification Search
CPC ............ A61B 1/00147; A61B 1/00151; A61B 1/00154; A61B 1/0002; A61B 2560/238
See application file for complete search history.

(56) References Cited

FOREIGN PATENT DOCUMENTS

| | | |
|---|---|---|
| JP | 2014-004268 A | 1/2014 |
| JP | 2014-064686 A | 4/2014 |

OTHER PUBLICATIONS

International Search Report dated Jul. 4, 2017 issued in PCT/JP2017/015438.

\* cited by examiner

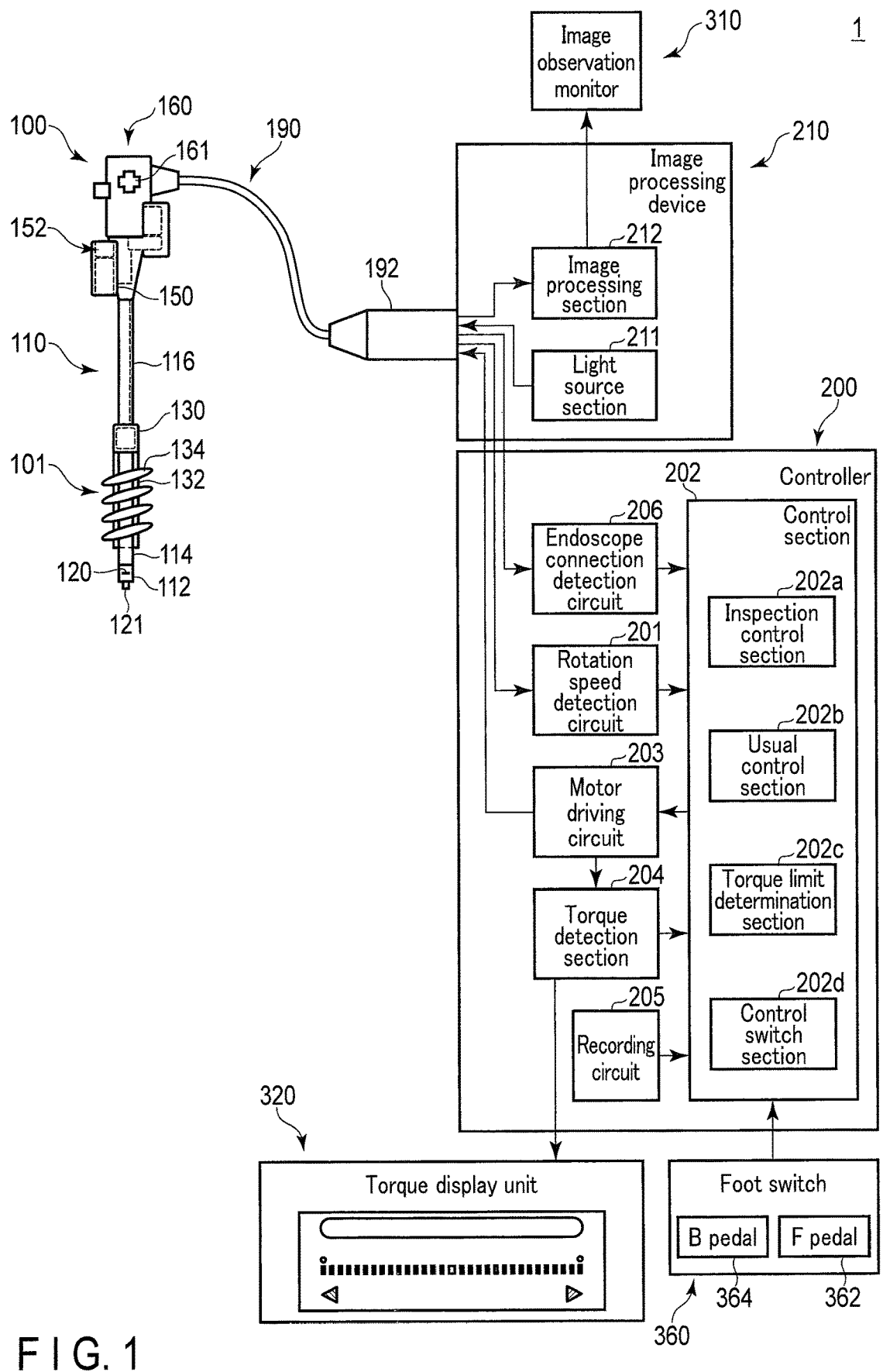
F I G. 1

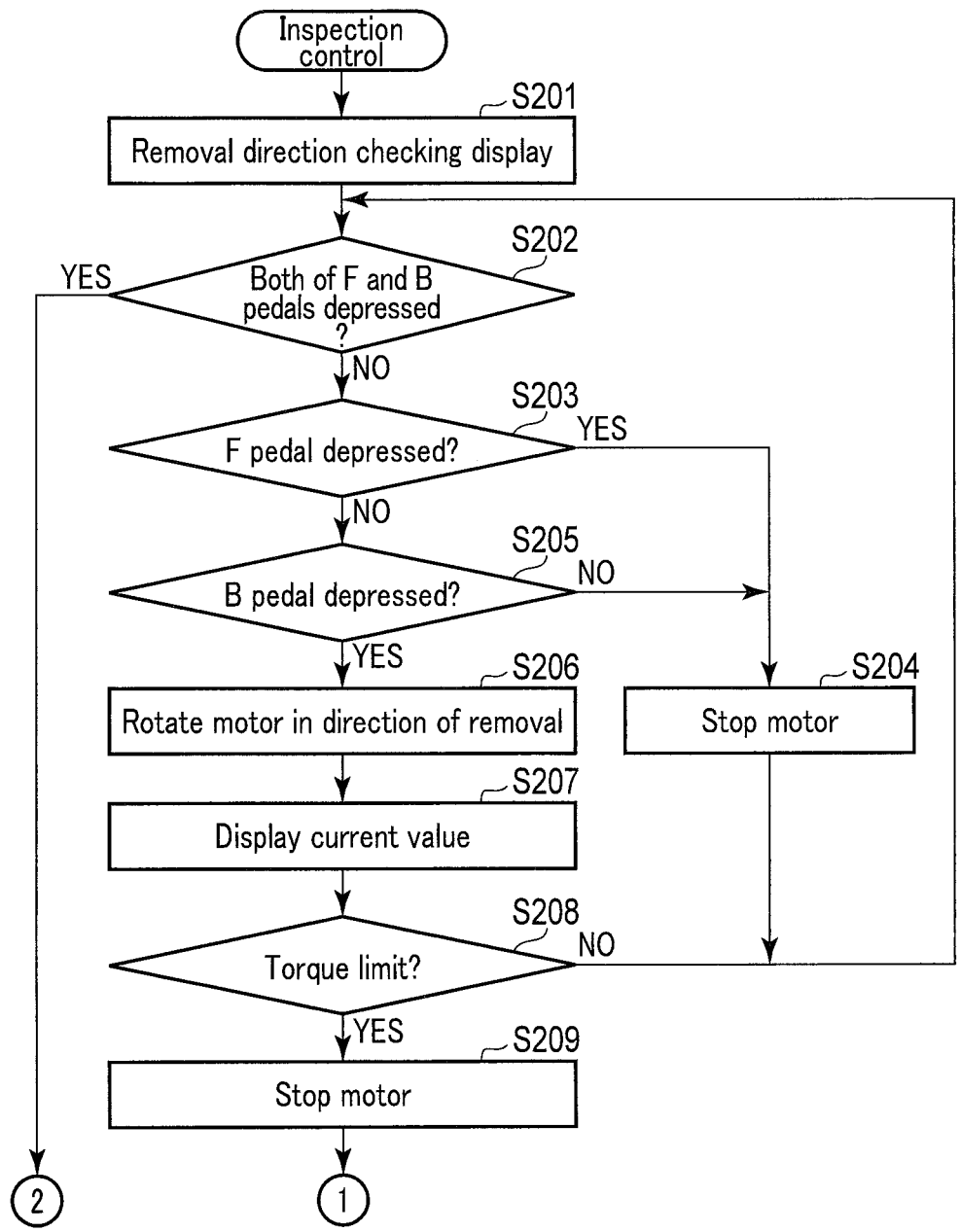
F I G. 3A

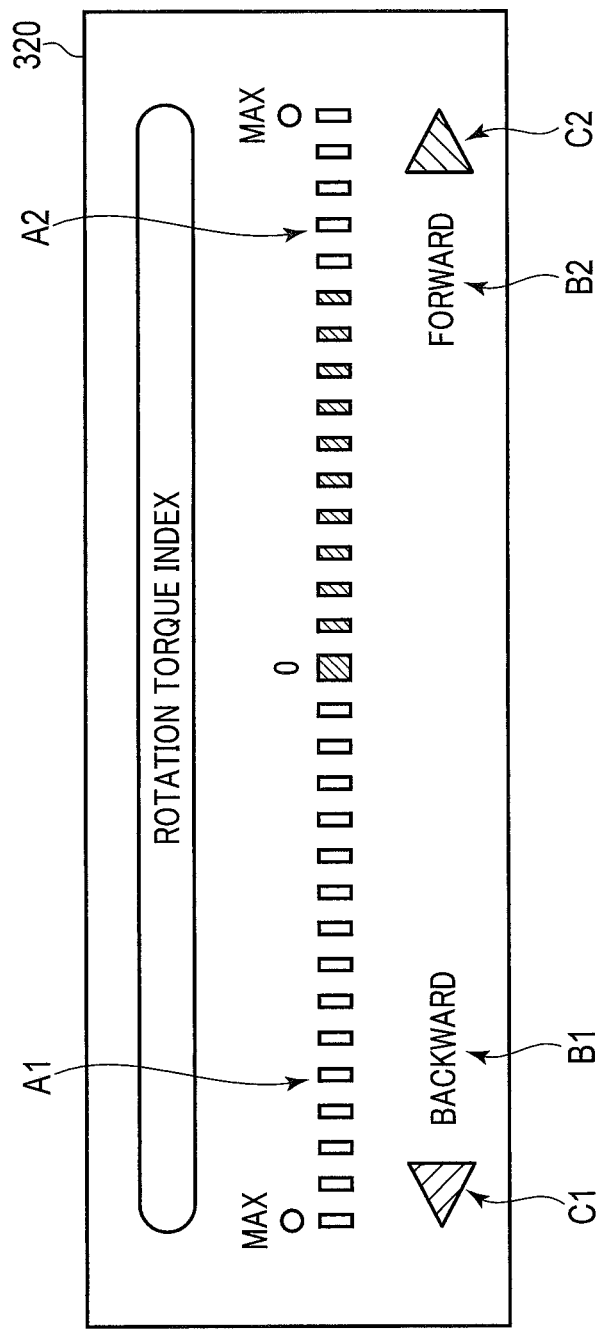
F I G. 4

CONTROLLER AND INSERTION APPARATUS

CROSS-REFERENCE TO RELATED APPLICATIONS

This application is a Continuation Application of PCT Application No. PCT/JP2017/015438, filed Apr. 17, 2017 and based upon and claiming the benefit of priority from prior Japanese Patent Application No. 2016-083014, filed Apr. 18, 2016, the entire contents of all of which are incorporated herein by reference.

BACKGROUND OF THE INVENTION

1. Field of the Invention

The present invention relates generally to a controller which controls the operation of a self-propelled mechanism comprised in an endoscope, and an insertion apparatus comprising the endoscope and the controller.

2. Description of the Related Art

In general, an insertion section of an insertion apparatus, such as an endoscope apparatus, is inserted into, for example, a lumen. One type of such an insertion apparatus inserted into a lumen which is known is a self-propelled insertion apparatus.

For example, the endoscope apparatus disclosed in Jpn. Pat. Appln. KOKAI Publication No. 2007-307241 is a rotary, self-propelled endoscope apparatus. In such a rotary, self-propelled endoscope apparatus, a rotating cylindrical body called a power spiral tube, in which a spiral-shaped fin is formed on an outer circumferential face of an insertion section, for example, is provided. When the rotating cylindrical body rotates, the fin formed on the rotating cylindrical body contacts an inner wall of the lumen, thus generating a propulsion force. By this propulsion force, the insertion section is propelled by itself in the direction of insertion or the direction of removal.

In the living body introduction apparatus disclosed in Jpn. Pat. Appln. KOKAI Publication No. 2014-64686, which is a rotary, self-propelled endoscope, the state of the apparatus is inspected before observation is started. This living body introduction apparatus is configured to check whether or not a lubricant is properly applied to a spiral tube before the start of the observation. That is, this living body introduction apparatus actually rotates the spiral tube, and determines whether or not a lubricant is properly applied according to the magnitude of a drive current of the motor at that time. This living body introduction apparatus shifts to an observation task only when it is determined that the apparatus is in a normal state, in which a lubricant is properly applied.

BRIEF SUMMARY OF THE INVENTION

According to an aspect of the present invention, a controller controls an operation of a self-propelled mechanism of an endoscope comprising an elongated insertion section and the self-propelled mechanism, the self-propelled mechanism generating a force that inserts the insertion section into or removes the insertion section from a subject. The controller includes an inspection control section which controls an inspection operation of the self-propelled mechanism; a usual control section which controls a usual operation of the self-propelled mechanism to insert the insertion section into or remove the insertion section from the subject; an endoscope connection detection circuit which detects that the endoscope has been connected; and a control switch section which, upon determining whether or not the inspection operation is performed for the endoscope at the time of the connection of the endoscope, causes the usual control section to perform the usual operation when the inspection operation is performed, and causes the inspection control section to perform the inspection operation and then causes the usual control section to perform the usual operation when the inspection operation is not performed.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 schematically shows a configuration example of an insertion apparatus according to a first embodiment.

FIG. 3A is a flowchart showing an example of an operation of an inspection control.

FIG. 4 is a diagram illustrating a display on a torque display unit.

DETAILED DESCRIPTION OF THE INVENTION

First Embodiment

Figure 2:
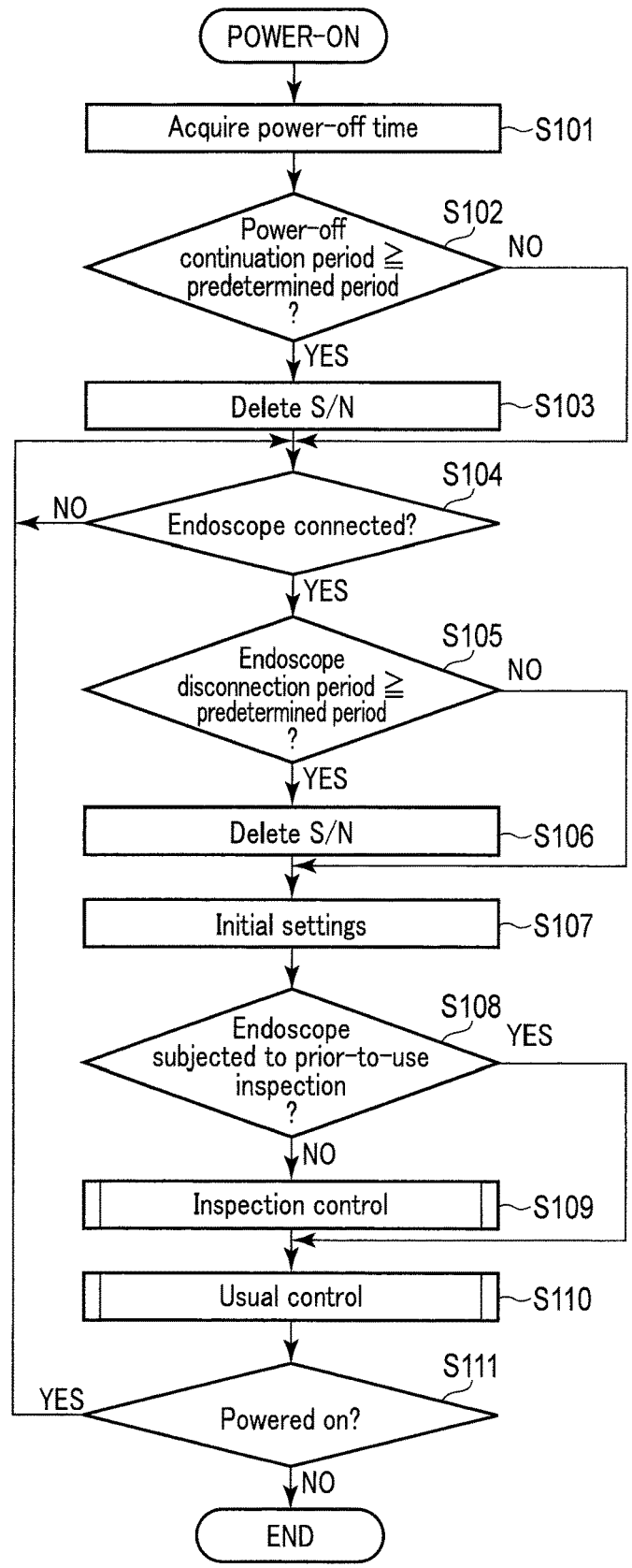
FIG. 2 is a flowchart showing an example of an operation of the insertion apparatus according to the first embodiment.

The first embodiment of the present invention will be described with reference to the accompanying drawings.

[Configuration of Insertion Apparatus]

FIG. 1 schematically shows a configuration of an endoscope system as an example of an insertion apparatus according to an embodiment of the present invention. As shown in FIG. 1, an insertion apparatus 1 includes an endoscope 100, a controller 200, an image processing device 210, an image observation monitor 310, a torque display unit 320, and a foot switch 360.

The endoscope 100 is a rotational, self-propelled endoscope, and includes an insertion section 110. The insertion section 110 is in an elongated shape, and is configured to be inserted into a living body. The endoscope 100 includes a control body 160 for performing various manipulations on the endoscope 100. The control body 160 is held by a user. Herein, a side distal to the insertion section 110 will be referred to as a distal side. Also, a side on which the control body 160 of the insertion section 110 is provided will be referred to as a proximal side. A direction running from the distal side toward the proximal side of the insertion section 110 will be referred to as a longitudinal direction. A control body 160 of the endoscope 100 and an image processing device 210 are connected via a universal cable 190. A connector 192 is provided at an end portion of the universal cable 190, and the connection between the image processing device 210 and the universal cable 190 is provided by the connector 192. The image processing device 210 and the controller 200 are connected, and the endoscope 100 and the controller 200 are connected via the image processing device 210.

The insertion section 110 includes a rigid distal section 112, a bending section 114, and an insertion tube 116. The rigid distal section 112 is a section at the extremity of the distal end of the insertion section 110, and is configured not to be bent. The bending section 114 is a section formed on the proximal side of the rigid distal section 112, and is configured to be actively bent in response to manipulation on a manipulation section 161 provided in the control body 160. The insertion tube 116 is a section formed on the proximal side of the bending section 114, and is configured to be passively bent by an external force.

The rigid distal section 112 includes an image sensor 120 and an illumination lens 121. The image sensor 120 generates an image signal based on a subject image, for example, on the distal side of the insertion section 110. The image signal generated by the image sensor 120 is transmitted to the image processing device 210 via a signal line for image signals (not shown in the drawings) that passes through the insertion section 110 and the universal cable 190. The illumination lens 121 diffuses light guided from the image processing device 210 via an optical fiber (not shown in the drawings) that passes through the insertion section 110 and the universal cable 190, and emits the diffused light.

The insertion apparatus 1 according to the present embodiment comprises a self-propelled mechanism 101. That is, a rotation section 130 for transmitting a driving force of the motor 150 provided in the control body 160 is attached to the insertion tube 116 of the insertion section 110. Also, a power spiral tube 132, which is a rotating cylindrical body, is attached to a distal side of the rotation section 130. The power spiral tube 132 is formed in a cylindrical form using an elastic material such as rubber, resin, etc., and is rotatably attached to the insertion tube 116 around its longitudinal axis. A spiral-shaped fin 134 is provided on an outer circumferential face of the power spiral tube 132 so as to extend along the longitudinal axis of the power spiral tube 132. The power spiral tube 132 may be configured to be detachable from the rotation section 130.

The power spiral tube 132 is connected to a motor 150 provided as an actuator in the control body 160. The motor 150 is connected to the controller 200 via a signal line for actuator current signals (not shown in the drawings) that passes through the control body 160 and the universal cable 190.

The motor 150 is operated by a manipulation which makes use of the foot switch 360. The rotational force of the motor 150 is transmitted to the rotational section 130. Thereby, the fin 134 provided on the power spiral tube 132 rotates around the longitudinal axis.

When the fin 134 rotates in contact with a wall, such as an inner wall of a lumen, a propulsion force that propels the insertion section 110 by itself is generated. In the small intestine or the large intestine, for example, the fin 134 crawls along the folds on the inner wall of the small intestine or the large intestine, and thereby a propulsion force acts on the insertion section 110. By this propulsion force, the insertion section 110 is propelled by itself. The self-propulsion of the insertion section 110 assists in the tasks of insertion and removal of the insertion section 110 by the user. In the explanation that follows, the direction of rotation of the motor 150 that propels the insertion section 110 toward the distal side will be referred to as a "normal direction" ("insertion direction"), and the direction of rotation of the motor 150 that propels the insertion section 110 toward the proximal side will be referred to as a "reverse direction" ("removal direction").

A pulse generating section 152 is provided in the motor 150. The pulse generating section 152 generates a pulse signal (rotation speed signal) according to a rotation speed of the motor 150. The rotation speed signal is transmitted to the controller 200 via a rotation speed signal line (not shown in the drawings) that passes through the universal cable 190.

The image observation monitor 310 includes a general display element such as a liquid crystal display. The image observation monitor 310 displays an endoscopic image based on an image signal obtained by, for example, the image sensor 120.

The foot switch 360 includes a FORWARD (F) pedal 362 and a BACKWARD (B) pedal 364. The F pedal 362 is a pedal depressed by the user when the user wants to make the motor 150 rotate in the normal direction. The B pedal 364 is a pedal depressed by the user when the user wants to make the motor 150 rotate in the reverse direction. Each of the F pedal 362 and the B pedal 364 is configured in such a manner that the amount of the depression is detected.

The torque display unit 320 is a display device configured using a display element such as an LED, and provides a display based on a display signal input from the torque detection section 204.

The controller 200 controls each section of the insertion apparatus 1. The controller 200 includes a rotation speed detection circuit 201, a control section 202, a motor driving circuit 203, a torque detection section 204, a recording circuit 205, and an endoscope connection detection circuit 206.

The rotation speed detection circuit 201 acquires a rotation speed signal input from the pulse generating section 152 every predetermined sampling interval. The rotation speed detection circuit 201 transmits the acquired rotation speed signal to the control section 202.

The control section 202 detects the depression of the F pedal 362 or the B pedal 364 by the user and the amount of the depression. The control section 202 supplies, to the motor driving circuit 203, a motor current that alters the rotation speed according to the amount of the depression of the F pedal 362 or the B pedal 364, using the rotation speed signal as a feedback signal. That is, the control section 202 calculates an instruction value based on a difference between the current motor speed and the target motor speed, and transmits the calculated instruction value to the motor driving circuit 203.

The motor driving circuit 203 is configured by, for example, a driver amplification circuit. The motor driving circuit 203 drives the motor 150 based on the instruction value. Thereby, the motor 150 rotates in the normal direction at a rotation speed corresponding to the amount of depression of the F pedal 362. The motor 150 rotates in the reverse direction at a rotation speed corresponding to the amount of depression of the B pedal 364.

The torque detection section 204 as a motor current detection section normalizes the current value of the motor current output from the motor driving circuit 203, and outputs a signal of the normalized current value as a display signal. The magnitude of the torque calculated based on the motor current may be normalized. Also, the torque detection section 204 transmits a signal corresponding to the magnitude of the motor current to the control section 202.

The recording circuit 205 is a recording medium that retains its contents with the power turned off, such as a flash memory, and records data such as programs for operating the controller 200 and torque limit values. The recording circuit 205 is not limited to a semiconductor memory, and may be, for example, a magnetic or optical medium. That is, each recording medium may bear the function of the recording circuit 205 as a recording section.

The endoscope connection detection circuit 206 is a circuit configured to detect whether or not the endoscope 100 is connected to the image processing device 210. The endoscope connection detection circuit 206 transmits information on the connection state of the endoscope 100 to the control section 202.

The control section 202 functions as an inspection control section 202a, a usual control section 202b, a torque limit determination section 202c, and a control switch section 202d.

The inspection control section 202a controls an inspection operation. The inspection operation is a control performed to cause the user to conduct an operation inspection of the endoscope 100. The usual control section 202b controls a usual operation. The usual operation is an operation performed by the self-propelled mechanism 101 to insert or remove the insertion section 110 into or from the subject during observation.

The torque limit determination section 202c determines whether or not a torque limit is to be placed on the motor 150, by determining whether or not a magnitude of a motor current output from the torque detection section 204 exceeds a torque limit value, which is a predetermined current threshold value. The torque limit determination section 202c determines that a torque limit is to be placed on the motor 150 when it is determined that the motor current exceeds a torque limit value. Torque limiting is a process of stopping the control section 202 from supplying a motor current to the motor driving circuit 203, thus suppressing a torque applied to the motor 150. When a torque limit is placed on the motor 150 that is rotating in the removal direction, the motor 150 stops the rotation in the removal direction. When a torque limit is placed on the motor 150 that is rotating in the insertion direction, the motor 150 stops the rotation in the insertion direction.

The control switch section 202d performs a control to switch between an inspection control performed by the inspection control section 202a and a usual control performed by the usual control section 202b.

The image processing device 210 includes a light source section 211 and an image processing section 212. The light source section 211 includes, for example, a white LED or a xenon lamp, and inputs light to an optical fiber (not shown in the drawings) in the universal cable 190. This light is emitted from the illumination lens 121.

The image processing section 212 acquires an image signal from the image sensor 120 via the insertion section 110 and the universal cable 190. The image processing section 212 performs image processing on the acquired image signal. The image processing section 212 transmits the processed image signal to the image observation monitor 310, and causes the image observation monitor 310 to display an endoscopic image.

<Outline of Operation of Insertion Apparatus>

An operation of an insertion apparatus 1 according to the embodiment of the present embodiment will be explained. In the present embodiment, a self-propelled mechanism 101 is inspected by activating the insertion apparatus 1. Herein, the inspection is conducted to check whether or not the torque limiting functions appropriately. In the present embodiment, the rotation section 130 is controlled so as to rotate at a rotation speed corresponding to the amount of depression of the pedal of the foot switch 360. Accordingly, when the rotation of the rotation section 130 is prevented by the depression of the pedal of the foot switch 360, a current supplied to the motor 150 is controlled in such a manner that a torque generated in the motor 150 increases so as to maintain a predetermined rotation speed. In the present embodiment, torque limiting functions in such a manner that the rotation of the rotation section 130 is stopped when the torque generated in the motor 150 reaches a predetermined value or above. The inspection at the time of activation is conducted to check whether or not the torque limiting functions normally. In the case of normal functioning, information indicating said normal functioning is recorded in the recording circuit 205, together with identification information that individually identifies the endoscope 100, such as a serial number (S/N) of the endoscope 100. The insertion apparatus 1 can be used in actuality after the inspection is ended. When the endoscope 100 is detached from the image processing device 210, or is powered off, the endoscope 100 operates in the following manner. That is, if the duration of time for which the endoscope 100 is detached or powered off is lengthy, the inspection of the self-propelled mechanism 101 is conducted again. On the other hand, if the duration of time is short, the inspection of the self-propelled mechanism 101 is not conducted.

<Details of Operation of Insertion Apparatus>

FIG. 2 is a flowchart showing an example of operation of the insertion apparatus 1. The operation shown in FIG. 2 is controlled by the controller 200. This operation is started when the power supply of the insertion apparatus 1 is turned on, for example. In parallel with the operation shown in FIG. 2, a process of displaying an endoscopic image based on an image signal obtained by the image sensor 120 on the image observation monitor 310 is performed.

In step S101, the control section 202 checks the time when the power supply was turned off last time. In the present embodiment, the time is periodically recorded in the recording circuit 205 while the power is supplied to the insertion apparatus 1. Accordingly, the last time recorded in the recording circuit 205 is regarded as the time when the power supply was turned off.

In step S102, the control section 202 determines whether or not the period of time during which the power-off state continues is equal to or longer than a predetermined period of time. If the power-off continuation period is not equal to or longer than a predetermined period of time, the processing advances to step S104. On the other hand, when the power-off continuation period is equal to or longer than a predetermined period of time, the processing advances to step S103.

In step S103, the control section 202 deletes the serial number of the endoscope 100 recorded in the recording circuit 205. Subsequently, the processing advances to step S104.

In step S104, the control section 202 determines whether or not the endoscope 100 is connected to the image processing device 210. If the connection is not made, the processing stands by, repeating step S104. On the other hand, if the endoscope 100 is connected to the image processing device 210, the processing advances to step S105.

In step S105, the control section 202 determines whether or not the period of time during which the endoscope 100 is not connected to the image processing device 210 is equal to or longer than a predetermined period of time. If the disconnection period is not equal to or longer than the predetermined period of time, the processing advances to step S107. On the other hand, if the disconnection period is equal to or longer than the predetermined period of time, the processing advances to step S106.

In step S106, the control section 202 deletes the serial number of the endoscope 100 recorded in the recording circuit 205. Subsequently, the processing advances to step S107. In this manner, if the power-off continuation period is equal to or longer than a predetermined period of time, or if the disconnection period is equal to or longer than a predetermined period of time, the serial number of the endoscope 100 recorded in the recording circuit 205 is deleted. On the other hand, if the power-off continuation period is shorter than a predetermined period of time, and if the disconnection period is shorter than a predetermined period of time, the serial number of the endoscope 100 subjected to the previous prior-to-use inspection recorded in the recording circuit 205 is maintained.

In step S107, the control section 202 performs various initial settings.

In step S108, the control section 202 reads the serial number recorded in the recording circuit 205 and the serial number of the connected endoscope 100, and compares the serial numbers. Based on the comparison result, the control section 202 determines whether or not a prior-to-use inspection has been conducted for the connected endoscope 100. For example, if the serial number recorded in the recording circuit 205 matches the serial number of the connected endoscope 100, it is determined that the prior-to-use inspection has been conducted. On the other hand, when the serial numbers do not match, or a serial number is not recorded in the recording circuit 205, it is determined that a prior-to-use inspection has not been conducted. Accordingly, the threshold value used in determining the power-off continuation period in step S102 and the threshold value used in determining the disconnection period of the endoscope 100 in step S105 are threshold values for adjusting the period of time during which it is determined that the prior-to-use inspection is conducted. These threshold values may be suitably adjusted. If the prior-to-use inspection has been conducted, the processing advances to step S110. On the other hand, if the prior-to-use inspection has not been conducted, the processing advances to step S109.

In step S109, the control section 202 performs an inspection control, which includes a prior-to-use inspection. The inspection control will be described in detail later. After the inspection control, the processing advances to step S110.

In step S110, the control section 202 performs a usual control that allows the insertion apparatus 1 to perform observation. The usual control will be described in detail later. After the usual control, the processing advances to step S111. In step S111, the control section 202 determines whether or not the power is supplied to the insertion apparatus 1. If the power is supplied, the processing returns to step S104. On the other hand, if the power supply is turned off, the processing is brought to an end.

Figure 3B:
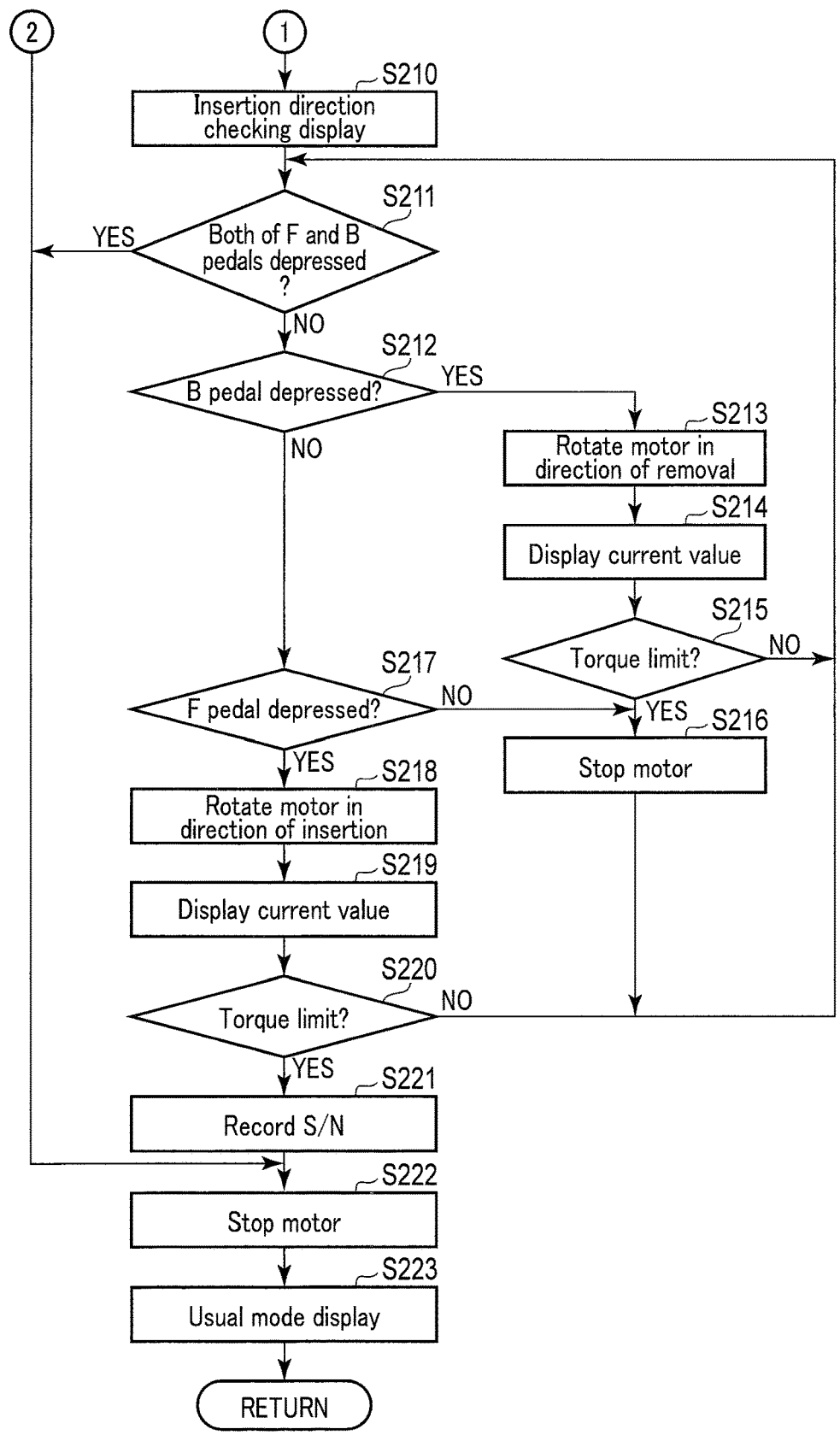
FIG. 3B is a flowchart showing an example of an operation of the inspection control.

The inspection control performed in step S109 will be explained with reference to the flowcharts shown in FIGS. 3A and 3B. In the inspection control, a removal direction check process to check the operation of the self-propelled mechanism 101 with regard to the removal direction is performed, and then an insertion direction check process to check the operation of the self-propelled mechanism 101 with regard to the insertion direction is performed.

In step S201, the control section 202 causes the torque display unit 320 to provide a removal direction checking display.

The display by the torque display unit 320 will be explained with reference to FIG. 4. FIG. 4 shows an example of display of the torque of the motor 150 using a level meter. On the display screen of the torque display unit 320, a removal direction scale indicator A1, an insertion direction scale indicator A2, a removal direction (BACKWARD) character indicator B1, an insertion direction (FORWARD) character indicator B2, an arrow indicator C1 regarding the removal direction, and an arrow indicator C2 regarding the insertion direction are provided. Each indicator includes, for example, an LED.

The removal direction scale indicator A1 is provided to the left of the "0" marking. The removal direction scale indicator A1 includes 15-level marking lamps, which are sequentially lit up in accordance with the magnitude of the motor current that rotates the motor 150 in the reverse direction. On the other hand, the insertion direction scale indicator A2 is provided to the right of the "0" marking. As in the removal direction scale indicator A1, the insertion direction scale indicator A2 includes 15-level marking lamps, which are sequentially lit up in accordance with the magnitude of the motor current that rotates the motor 150 in the normal direction. The "0" marking is constantly lit up, for example. When the motor 150 rotates in the normal direction, for example, a number of marking lamps of the insertion direction scale indicator A2 corresponding to the magnitude of the motor current are lit up, as shown in FIG. 4.

The removal direction character indicator B1 is provided to display the characters "BACKWARD", and is in either a lit-up state, an "off" state, or a flashing state. The removal direction character indicator B1 is lit up during the usual control, flashes during the removal direction checking display, and is turned off during the insertion direction checking display that will be explained later. The insertion direction character indicator B2 is provided to display the characters "FORWARD", and is in either a lit-up state, an "off" state, or a flashing state. The insertion direction character indicator B2 is lit up during the usual control, turned off during the removal direction checking display, and flashes during the insertion direction checking display that will be explained later.

The arrow indicator C1 is in either a lit-up state, an "off" state, or a flashing state, in a manner similar to the removal direction character indicator B1. The arrow indicator C1 is lit up during the usual control, flashes during the removal direction checking display, and is turned off during the insertion direction checking display that will be explained later. The arrow indicator C2 is in either a lit-up state, an "off" state, or a flashing state, in a manner similar to the insertion direction character indicator B2. The arrow indicator C2 is lit up during the usual control, is turned off during the removal direction checking display, and flashes during the insertion direction checking display that will be explained later.

Next, the removal direction checking display will be explained. As described above, in the removal direction checking display, both the removal direction character indicator B1 and the arrow indicator C1 flash, and both the insertion direction character indicator B2 and the arrow indicator C2 are turned off. Since only the indicators on the removal direction side flash in the removal direction checking display, the user can recognize that an inspection should be conducted with regard to the removal direction.

In the inspection conducted by the user that will be explained below, the rotation section 130 is held by the user's hand, for example, to suppress its rotation. In the present embodiment, the rotation section 130 is controlled so as to rotate at a rotation speed corresponding to the amount of depression of the pedal of the foot switch 360. Accordingly, when the pedal of the foot switch 360 is depressed while the rotation section 130 is held to suppress its rotation, the value of the current supplied to the motor 150 increases to achieve a rotation speed corresponding to the amount of the depression of the pedal. That is, the torque generated in the motor 150 increases. When the value of the motor current reaches a predetermined value or above, a torque limit is placed, and the motor 150 is controlled to stop the rotation.

In step S202, the control section 202 determines whether or not the F pedal 362 and the B pedal 364 are simultaneously depressed. If the F pedal 362 and the B pedal 364 are simultaneously depressed, the inspection control is forcibly brought to an end. If it is determined that the F pedal 362 and the B pedal 364 are simultaneously depressed, the processing advances to step S222. On the other hand, if it is determined that the F pedal 362 and the B pedal 364 are not simultaneously depressed, the processing advances to step S203.

In step S203, the control section 202 determines whether or not the F pedal 362 is depressed. If it is determined that the F pedal 362 is depressed, the processing advances to step S204. In step S204, the control section 202 stops the motor current supply to the motor driving circuit 203, and stops the rotation of the motor 150. Subsequently, the processing returns to step S202. That is, the insertion section 110 does not move in the insertion direction during the removal direction check process.

If it is determined in step S203 that the F pedal 362 is not depressed, the processing advances to step S205. In step S205, the control section 202 determines whether or not the B pedal 364 is depressed. If it is determined that the B pedal 364 is not depressed, the processing advances to step S204. Thereby, the motor 150 stops, and the processing returns to step S202.

If it is determined in step S205 that the B pedal 364 is depressed, the processing advances to step S206. In step S206, the control section 202 causes the motor driving circuit 203 to supply a motor current to the motor 150 in such a manner that the fin 134 rotates in the reverse direction at a rotation speed corresponding to the amount of depression of the B pedal 364 by the user. Subsequently, the processing advances to step S207.

In step S207, the torque detection section 204 generates a display signal based on a value of the motor current output from the motor driving circuit 203, and causes the torque display unit 320 to provide a display based on the generated display signal. That is, the torque detection section 204 lights up a larger number of marking lamps of the removal direction scale indicator A1 as the value of the motor current increases. Subsequently, the processing advances to step S208.

In step S208, the control section 202 determines whether or not the value of the motor current acquired from the torque detection section 204 exceeds a torque limit value. That is, the control section 202 determines whether or not a torque limit is to be placed on the current supplied to the motor 150. If it is determined that a torque limit is not to be placed, namely, the value of the motor current acquired from the torque detection section 204 is less than the torque limit value, the processing returns to step S202.

If it is determined in step S208 that the torque limit is to be placed, namely, the magnitude of the torque input to the torque limit determination section 202c is equal to or greater than the torque limit value, the processing advances to step S209. In step S209, the control section 202 stops the motor current supply to the motor driving circuit 203, and stops the rotation of the motor 150. Subsequently, the processing advances to step S210.

Since the processing from step S202 to step S208 is repeated until the torque limit is placed, as described above, the self-propelled mechanism 101 operates only in the removal direction, and is prohibited from operating in the insertion direction.

In step S210, the control section 202 causes the torque display unit 320 to provide an insertion direction checking display. The insertion direction checking display is a display indicating that a torque limiting inspection regarding the insertion direction is started.

The insertion direction checking display will be explained below. In the insertion direction checking display, both the removal direction character indicator B1 and the arrow indicator C1 are turned off, and both the insertion direction character indicator B2 and the arrow indicator C2 will flash, as described above. That is, since only the indicators on the insertion direction side flash in the insertion direction checking display, the user can recognize that an inspection should be conducted with regard to the insertion direction.

In step S211, the control section 202 determines whether or not the F pedal 362 and the B pedal 364 are simultaneously depressed. If it is determined that the F pedal 362 and the B pedal 364 are simultaneously depressed, the processing advances to step S222. On the other hand, if it is determined that the F pedal 362 and the B pedal 364 are not simultaneously depressed, the processing advances to step S212.

In step S212, the control section 202 determines whether or not the B pedal 364 is depressed. If the B pedal 364 is not depressed, the processing advances to step S217. On the other hand, if the B pedal 364 is depressed, the processing advances to step S213. In step S213, the control section 202 rotates the motor 150 in the removal direction. That is, the control section 202 causes the motor driving circuit 203 to output a motor current. By this motor current, the motor 150 rotates in the reverse direction. The rotation operation in the removal direction is permitted even during the check of the insertion direction.

In step S214, the torque detection section 204 generates a display signal based on the value of the motor current output from the motor driving circuit 203, and causes the torque display unit 320 to provide a display based on the generated display signal. That is, the torque detection section 204 lights up a larger number of marking lamps of the removal direction scale indicator A1 as the value of the motor current increases. Subsequently, the processing advances to step S215.

In step S215, the control section 202 determines whether or not a torque limit is to be placed on the motor 150. If a torque limit is not to be placed, the processing returns to step S211. On the other hand, if a torque limit is to be placed, the processing advances to step S216. In step S216, the control section 202 stops the motor current supply to the motor driving circuit 203, and stops the rotation of the motor 150. Subsequently, the processing returns to step S211.

If it is determined in step S212 that the B pedal 364 is not depressed, the processing advances to step S217. In step S217, the control section 202 determines whether or not the F pedal 362 is depressed. If the F pedal 362 is not depressed, the processing advances to step S216. That is, the motor 150 stops, and the processing returns to step S211.

If it is determined in step S217 that the F pedal 362 is depressed, the processing advances to step S218. In step S218, the control section 202 rotates the motor 150 in the insertion direction. That is, the control section 202 causes the motor driving circuit 203 to output a motor current.

In step S219, the torque detection section 204 generates a display signal based on the value of the motor current output from the motor driving circuit 203, and causes the torque display unit 320 to provide a display based on the generated display signal. That is, the torque detection section 204 lights up a larger number of marking lamps of the insertion direction scale indicator A2 as the value of the motor current increases.

In step S220, the control section 202 determines whether or not a torque limit is to be placed on the motor 150. If a torque limit is not to be placed, the processing returns to step S211. If a torque limit is to be placed, the processing advances to step S221.

In step S221, the control section 202 records, in the recording circuit 205, a serial number of the endoscope 100 that is currently connected. Subsequently, the processing advances to step S222.

In step S222, the control section 202 stops the motor current supply to the motor driving circuit 203, and stops the rotation of the motor 150. In step S223, the control section 202 causes the torque display unit 320 to provide a usual mode display.

In the usual mode display, all of the removal direction character indicator B1, the arrow indicator C1, the insertion direction character indicator B2, and the arrow indicator C2 are lit up. That is, a display which differs from either the removal direction checking display or the insertion direction checking display is provided. Thereby, the user can recognize that the control has been shifted to the usual control.

By the processing in step S223, the inspection control is brought to an end, and the processing returns to the main processing explained with reference to FIG. 2. In the above-described manner, in the inspection control, it is confirmed that the torque limiting will function normally with regard to the removal direction and the insertion direction in this order.

Figure 5:
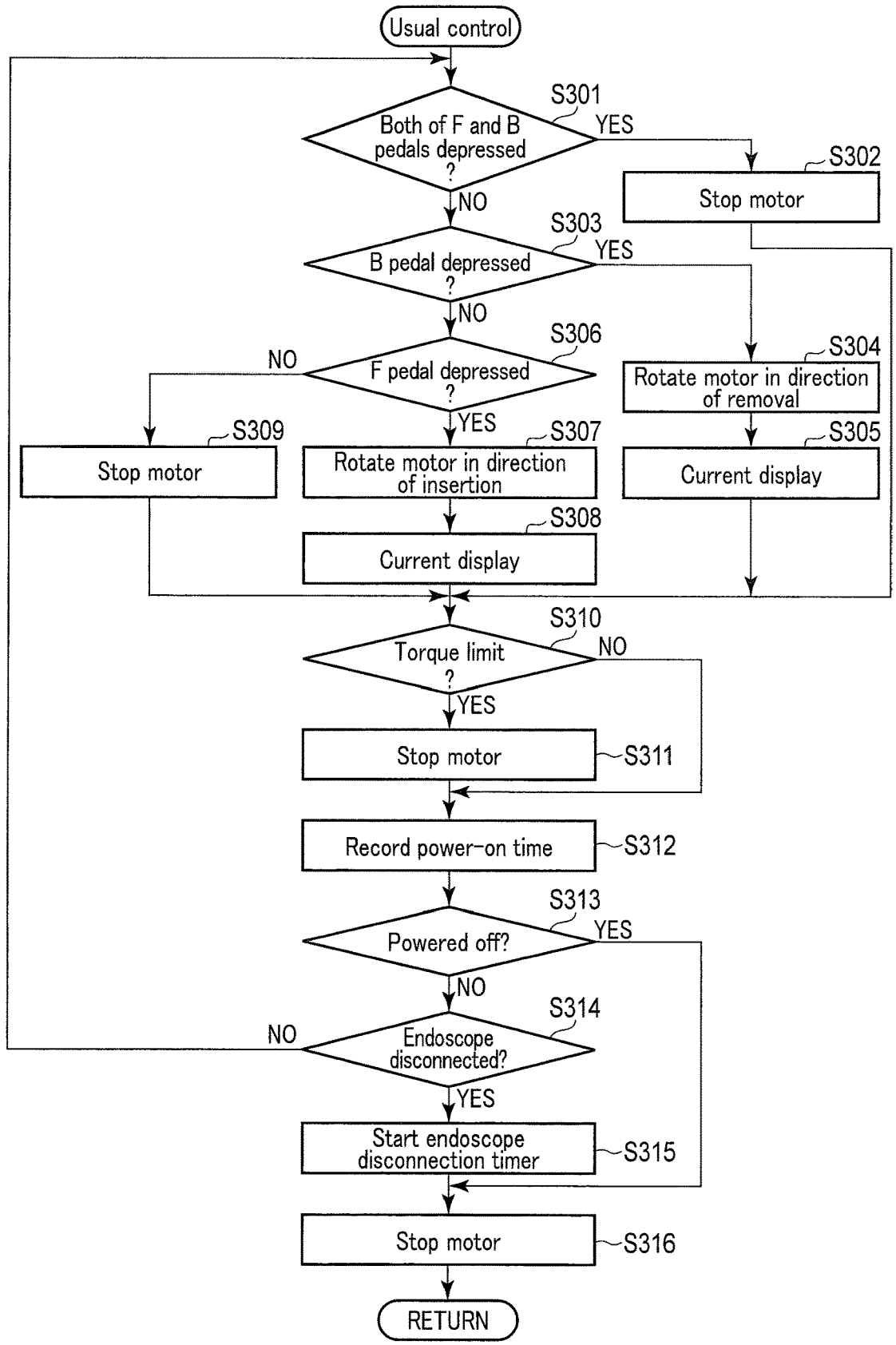
FIG. 5 is a flowchart showing an example of an operation of a usual control according to the first embodiment.

The usual control performed in step S110 will be explained with reference to the flowchart shown in FIG. 5.

In step S301, the control section 202 determines whether or not the F pedal 362 and the B pedal 364 are simultaneously depressed. If the F pedal 362 and the B pedal 364 are simultaneously depressed, the processing advances to step S302. In step S302, the control section 202 performs processing to stop the motor current output, and stops the rotation of the motor 150. Subsequently, the processing advances to step S310.

If it is determined in step S301 that the F pedal 362 and the B pedal 364 are not simultaneously depressed, the processing advances to step S303. In step S303, the control section 202 determines whether or not the B pedal 362 is depressed. If it is determined that the B pedal 362 is depressed, the processing advances to step S304. In step S304, the control section 202 performs an operation in the removal direction. That is, the control section 202 causes the motor driving circuit 203 to supply a motor current regarding the removal direction to the motor 150. Subsequently, in step S305, the torque detection section 204 generates a display signal based on the value of the motor current output from the motor driving circuit 203, and causes the torque display unit 320 to provide a display based on the generated display signal. Subsequently, the processing advances to step S310.

If it is determined in step S303 that the B pedal 362 is not depressed, the processing advances to step S306. In step S306, the control section 202 determines whether or not the F pedal 364 is depressed. If it is determined that the F pedal 364 is depressed, the processing advances to step S307. In step S307, the control section 202 performs an operation in the insertion direction. That is, the control section 202 causes the motor driving circuit 203 to supply a motor current regarding the insertion direction to the motor 150. Subsequently, in step S308, the torque detection section 204 generates a display signal based on the value of the motor current output from the motor driving circuit 203, and causes the torque display unit 320 to provide a display based on the generated display signal. Subsequently, the processing advances to step S310.

If it is determined in step S306 that the F pedal 364 is not depressed, the processing advances to step S309. In step S309, the control section 202 stops the motor current supply, and stops the rotation of the motor 150. Subsequently, the processing advances to step S310.

In step S310, the control section 202 determines whether or not a torque limit is to be placed. If a torque limit is not to be placed, the processing advances to step S312. If it is determined that a torque limit is to be placed, the processing advances to step S311. In step S311, the control section 202 stops the motor current supply, and stops the rotation of the motor 150. Subsequently, the processing advances to step S312.

In step S312, the control section 202 records, in the recording circuit 205, the current time as a time when the power is supplied. In this manner, the latest power-on time is recorded in the recording circuit 205. Accordingly, when the power supply is turned off, the last update time recorded in step S312 is used as the time when the power supply was turned off.

In step S313, the control section 202 determines whether the power supply of the insertion apparatus 1 is turned off. If it is determined that the power supply is turned off, the processing advances to step S316. On the other hand, if the power supply is not turned off, the processing advances to step S314.

In step S314, the control section 202 determines whether or not the connection between the endoscope 100 and the image processing device 210 is removed, namely, whether the endoscope 100 and the image processing device 210 are disconnected. If it is determined that the connection between the endoscope 100 and the image processing device 210 is maintained, the processing returns to step S301. On the other hand, if the connection between the endoscope 100 and the image processing device 210 is removed, the processing advances to step S315.

In step S315, the control section 202 starts an endoscope disconnection timer that measures the period of time during which the endoscope 100 and the image processing device 210 are disconnected. Subsequently, the processing advances to step S316.

In step S316, the control section 202 stops the motor current supply, and stops the rotation of the motor 150. Subsequently, the processing returns to the processing of the main flow explained with reference to FIG. 2.

For example, if the power supply is turned off, the control section 202 ends the usual control. In the determination in step S111 performed subsequent to the usual processing in step S110, the control section 202 determines that the power supply is not turned on. Thereby, the main flow shown in FIG. 2 is brought to an end. In this case, when the power supply of the controller 200 is turned on again, the control section 202 reads the last power-on time recorded in the recording circuit 205 in step S101. The control section 202 regards this recorded time as the time when the power supply was turned off. In step S102, the control section determines a power-off continuation period based on the time when the power supply was turned off.

When the endoscope 100 is detached from the image processing device 210 in the course of the usual control, the control section 202 starts the endoscope disconnection timer in step S315, and then ends the usual control. In the determination in step S111 performed subsequent to the usual processing in step S110, the control section 202 determines that the power is supplied to the insertion apparatus 1, and the processing advances to step S104. When the endoscope 100 is connected to the image processing device 210 again, the control section 202 determines an endoscope disconnection period in step S105, based on the measurement time obtained by the endoscope disconnection timer.

<Advantages of Insertion Apparatus>

In the inspection control of the insertion apparatus 1 according to the present embodiment, a removal direction check process is performed, and when an inspection is ended normally in the removal direction check process, an insertion direction check process is performed. Also, to permit the insertion section 110 to move only in the removal direction during the removal direction check process, the motor 150 is kept in a stopped state even when the F pedal 362 is depressed. Thereby, the insertion section 110 is not inserted into a lumen during the inspection.

When the insertion section 110 of the endoscope 100 is inserted into a subject for observation, the insertion section 110 is adjusted and twisted at various angles. Thereby, it is possible that the universal cable 190 may be twisted. For example, in the case of endoscopic retrograde cholangiopancreatography (ERCP), the endoscope 100, in particular, tends to become largely twisted. In such a case, the user may remove the universal cable 190 from the image processing device 210, thus eliminating the twist. In the present embodiment, when the universal cable 190 of the endoscope 100 is temporarily detached from the image processing device 210, and is reconnected after passage of a short duration of time, usual processing is performed, without performing inspection processing again. On the other hand, when the universal cable 190 is kept detached from the image processing device 210 for a long duration of time, inspection processing is performed at the time of reconnection. Thus, the functioning of the torque limit is confirmed in the inspection operation in the case of long-duration disuse; however, the inspection operation is omitted at the time of reconnection in the case of short-duration removal for elimination of the twist, for example. When the twist is eliminated, for example, it may be inconvenient to perform an inspection operation, due to the insertion section 110 being inserted into a subject.

In the above-described cases, it is supposed that the condition under which the serial number is maintained in the recording circuit 205 involves the disconnection state lasting for less than a few minutes.

In the event of a power failure, for example, the power supply to the insertion apparatus 1 may be temporarily stopped. Usually, the power supply is immediately resumed in such a case. In the present embodiment, an unnecessary inspection operation is omitted at the time of recovery from a short-duration power failure.

According to the insertion apparatus 1 of the present embodiment, it is possible to enhance the convenience for the user.

When the inspection operation does not need to be performed for a long period of time, the threshold value used in the determinations in steps S102 and step S105 may be increased, or the processing in steps S102 and S103 and the processing in steps S105 and S106 may be omitted.

<Modification>

The self-propelled mechanism may be any configuration. For example, the self-propelled mechanism may be configured in such a manner that a belt rotating in the longitudinal direction of the insertion section 110 is provided on an outer periphery of the insertion section 110.

In the above-described example, the determination as to whether or not to perform an inspection control is made based on both the period of time during which the endoscope 100 is detached from the image processing device 210 and the period of time during which the power supply is turned off; however, the configuration is not limited thereto. The determination as to whether or not to perform an inspection control may be made based on either the period of time during which the endoscope 100 is detached from the image processing device 210, or the period of time during which the power supply is turned off.

Second Embodiment

The second embodiment of the present invention will be explained. Herein, differences from the first embodiment will be described. The same symbols will be used to denote similar structural elements, and a description of such structural elements will be omitted. In the first embodiment, the control section 202 of the controller 200 determines whether or not a prior-to-use inspection of the endoscope 100 connected to the image processing device 210 has been conducted, based on the serial number of the endoscope 100 and the information recorded in the recording circuit 205 of the controller 200. In the present embodiment, on the other hand, information relating to a situation of a prior-to-use inspection is recorded in a memory provided in an endoscope 100, and a control section 202 of a controller 200 determines, based on this information, whether or not a prior-to-use inspection of the endoscope 100 connected to an image processing device 210 has been conducted.

Figure 6:
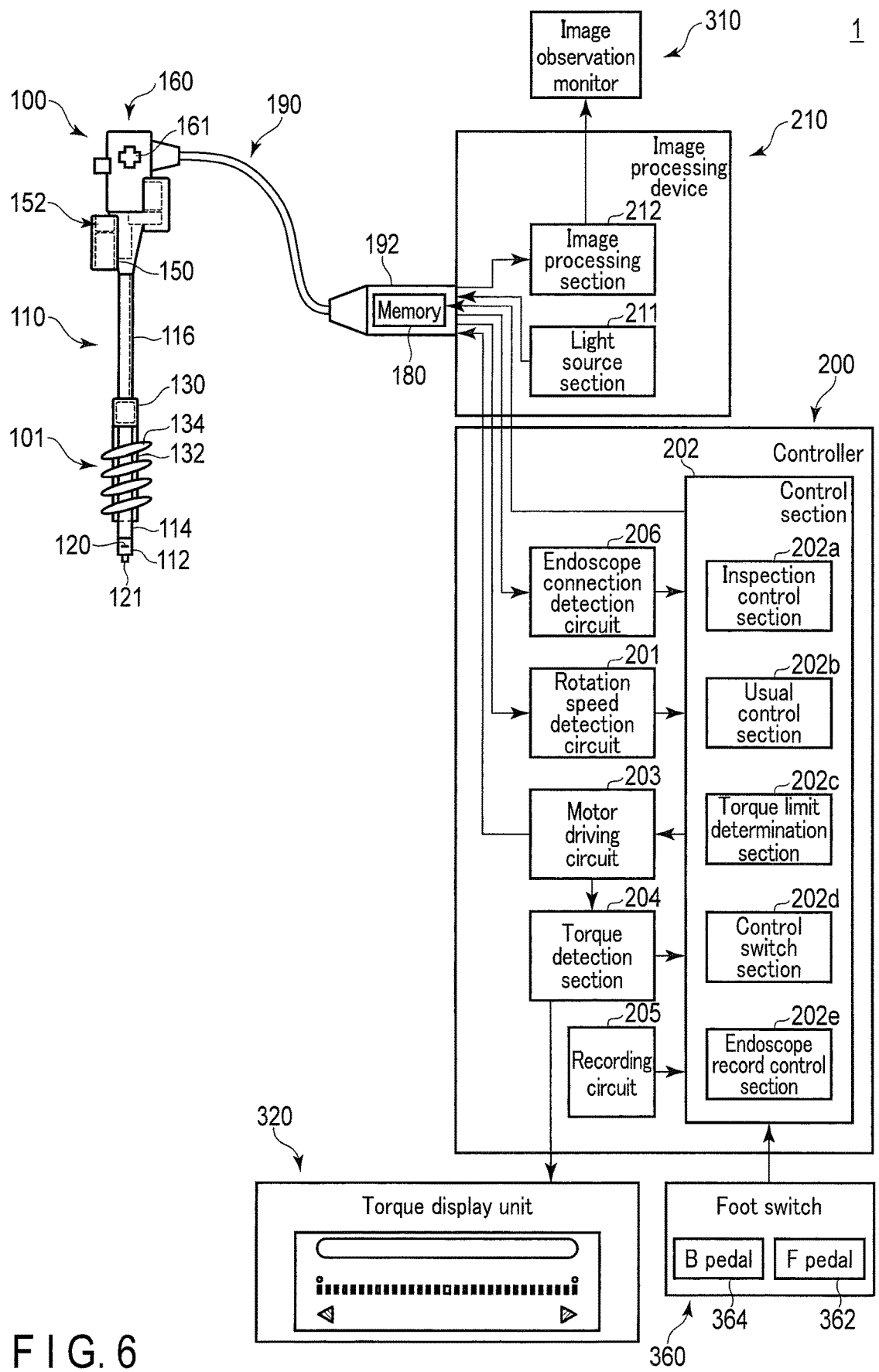
FIG. 6 schematically shows a configuration example of an insertion apparatus according to a second embodiment.

An outline of the configuration example of an insertion apparatus 1 according to the present embodiment is shown in FIG. 6. As shown in FIG. 6, a memory 180 is provided in the endoscope 100. FIG. 6 shows an example in which the memory 180 is provided in a connector 192; however, the memory 180 may be arranged at any position of the endoscope 100. For example, the memory 180 may be arranged in a control body 160.

In the present embodiment, the control section 202 of the controller 200 has the function as an endoscope record control section 202e. The endoscope record control section 202e controls an operation of recording in the memory 180 performed by the endoscope 100. The memory 180 records the time when the connection between the controller 200 and the endoscope 100 is removed, for example.

Figure 7:
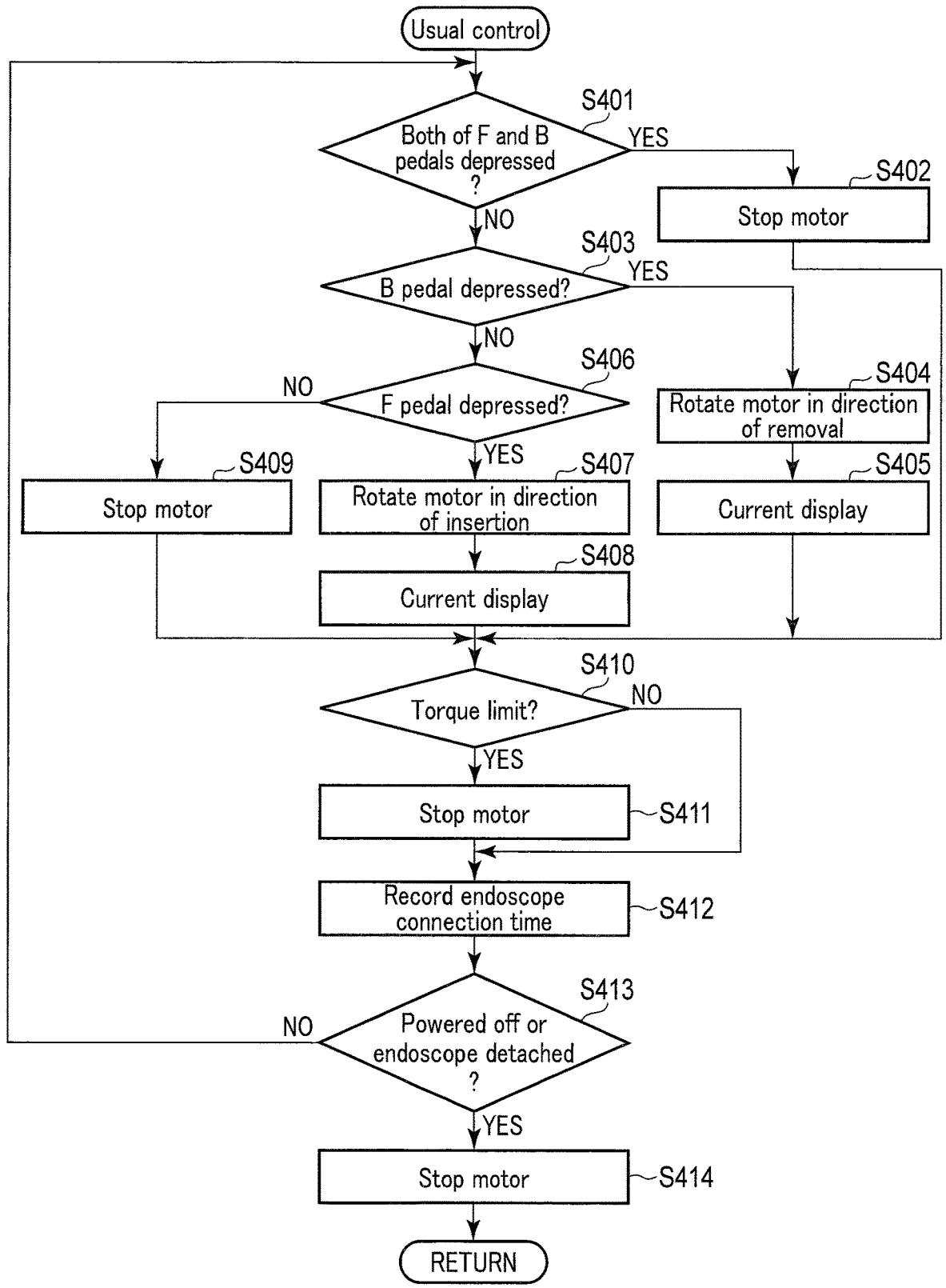
FIG. 7 is a flowchart showing an example of an operation of a usual control according to the second embodiment.

The usual control according to the present embodiment will be explained with reference to the flowchart shown in FIG. 7. The processing from step S401 to step S411 of the usual control according to the present embodiment is similar to the processing from step S301 to step S311 of the usual control according to the first embodiment explained with reference to FIG. 5. That is, the processing can be briefly explained as below.

In step S401, the control section 202 determines whether or not the F pedal 362 and the B pedal 364 are simultaneously depressed. If the F pedal 362 and the B pedal 364 are simultaneously depressed, the control section 202 stops the motor 150 in step S402. Subsequently, the processing advances to step S410.

If it is determined in step S401 that the F pedal 362 and the B pedal 364 are not simultaneously depressed, the control section 202 determines whether or not the B pedal 362 is depressed. If it is determined that the B pedal 362 is depressed, the control section 202 rotates the motor 150 in the removal direction in step S404. In step S405, the torque detection section 204 causes the torque display unit 320 to provide a display based on a display signal. Subsequently, the processing advances to step S410.

If it is determined in step S403 that the B pedal 362 is not depressed, the control section 202 determines in step S406 whether or not the F pedal 364 is depressed. If it is determined that the F pedal 364 is depressed, the control section 202 rotates the motor 150 in the insertion direction in step S407. In step S408, the torque detection section 204 causes the torque display unit 320 to provide a display based on a display signal. Subsequently, the processing advances to step S410.

If it is determined in step S406 that the F pedal 364 is not depressed, the control section 202 stops the motor current supply in step S409, and stops the rotation of the motor 150. Subsequently, the processing advances to step S410.

In step S410, the control section 202 determines whether or not a torque limit is to be placed. If a torque limit is not to be placed, the processing advances to step S412. If it is determined that a torque limit is to be placed, the control section 202 stops the motor 150 in step S411. Subsequently, the processing advances to step S412.

In step S412, the control section 202 causes the memory 180 of the endoscope 100 to record the current time as an endoscope connection time. In this manner, the latest time when the endoscope 100 and the controller 200 are connected is recorded in the memory 180.

In step S413, the control section 202 determines whether or not the power supply is turned off, or whether or not the endoscope 100 is detached from the image processing device 210. If the power supply is not turned off, and if the endoscope 100 is not detached from the image processing device 210, the processing returns to step S401. If the power supply is turned off, or if the endoscope 100 is detached from the image processing device 210, the processing advances to step S414.

In step S414, the control section 202 stops the output to the motor 150. In the above manner, the usual control is brought to an end.

Figure 8:
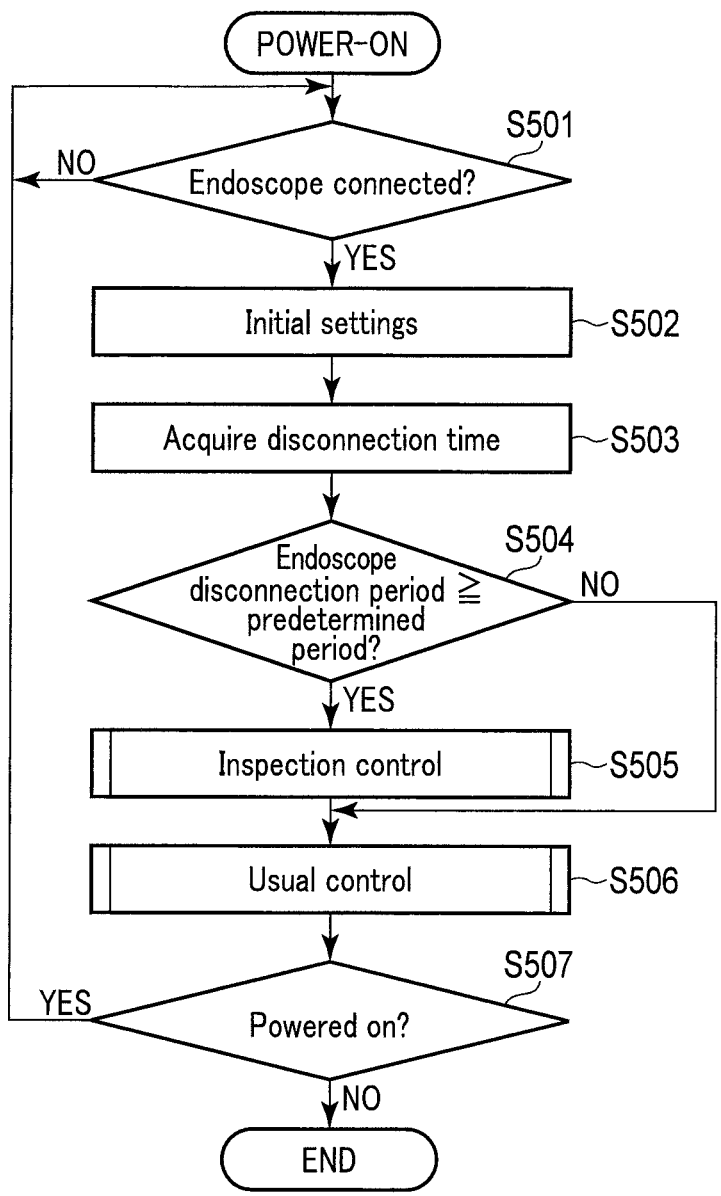
FIG. 8 is a flowchart showing an example of an operation of the insertion apparatus according to the second embodiment.

The main flow according to the present embodiment will be explained with reference to the flowchart shown in FIG. 8.

In step S501, the control section 202 determines whether or not the endoscope 100 is connected to the image processing device 210. If the connection is not made, the processing stands by, repeating step S501. If the connection is made, the processing advances to step S502.

In step S502, the control section 202 performs initial settings.

In step S503, the control section 202 reads the endoscope connection time recorded in the memory 180 of the endoscope 100, and regards this time as a disconnection time. The disconnection time is a time regarded as when the endoscope 100 was detached from the image processing device 210, or the time when the power supply of the controller 200 was turned off.

In step S504, the control section 202 determines whether or not the endoscope disconnection period, which is a duration of time for which the endoscope 100 is detached from the image processing device 210, is equal to or longer than a predetermined period of time, based on the disconnection time acquired in step S503. If the endoscope disconnection period is equal to or longer than the predetermined period of time, the processing advances to step S505. In step S505, the control section 202 performs an inspection control. The inspection control performed herein is similar to the inspection control performed in the first embodiment explained with reference to FIGS. 3A and 3B. The recording of the serial number in step S221 may be omitted. Subsequent to the inspection control, the processing advances to step S506. If it is determined in step S504 that the endoscope disconnection period is not equal to or longer than a predetermined period of time, the processing advances to step S506.

In step S506, the control section 202 performs the usual control explained with reference to FIG. 7. Subsequent to the usual control, the processing advances to step S507. That is, when the power supply is turned off, or when the endoscope 100 is detached from the image processing device 210, the processing advances to step S507.

In step S507, the control section 202 determines whether or not the power supply is turned on. If the power supply is turned on, the processing advances to step S501, and stands by until the endoscope 100 is reconnected to the image processing device 210. If the power supply is not turned on, the processing is brought to an end.

According to the present embodiment, it is possible to determine an endoscope disconnection period, based on the time recorded in the memory 180 of the endoscope 100. If the endoscope disconnection period is short, a usual control is performed, without performing an inspection control, and if the endoscope disconnection period is long, the usual control is performed after the inspection control. In this manner, it is possible in the present embodiment to obtain the same effect as can be obtained by the first embodiment.

<Modification>

The memory 180 may record a time when the inspection control is performed, and when the passage of time after the performance of the inspection control is shorter than a predetermined period of time, a usual control may be performed, without performing an inspection control.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A controller configured to be connected to a self-propelled mechanism of an endoscope, the endoscope comprising an elongated insertion section, the self-propelled mechanism having a spiral-shaped projection rotatably disposed relative to the insertion section for generating a force that inserts the insertion section into or removes the insertion section from a subject, the controller comprising:

at least one circuit configured to:
control an inspection operation of the self-propelled mechanism, the inspection operation including controlling, by the circuit, the self-propelled mechanism to inhibit the insertion of the insertion section and to permit the removal of the insertion section;
control a usual operation of the self-propelled mechanism, the usual operation including controlling, by the circuit, the self-propelled mechanism to permit both the insertion of the insertion section and the removal of the insertion section;
determine whether or not the inspection operation has been performed for the endoscope when the self-propelled mechanism of the endoscope has been connected to the controller; and
if the inspection operation has not been performed, perform the inspection operation and then perform the usual operation.

2. The controller according to claim 1, further comprising a memory that records identification information, wherein the at least one circuit is further configured to
read, from the endoscope, the identification information recorded in the endoscope that individually identifies the endoscope,
cause the memory to record the identification information of the self-propelled mechanism of the endoscope that is connected to the controller during the performance of the inspection operation after the inspection operation has been performed, and
compare the identification information recorded in the memory and the identification information of the self-propelled mechanism of the endoscope connected to the controller, and determine whether or not the inspection operation has been performed for the endoscope when the self-propelled mechanism of the endoscope has been connected to the controller.

3. The controller according to claim 2, wherein the at least one circuit is further configured to
delete the identification information recorded in the memory when a predetermined period of time has passed after the self-propelled mechanism of the endoscope has been detached from the controller, and
determine that the inspection operation has not been performed for the endoscope when the identification information is not recorded in the memory.

4. The controller according to claim 3, wherein the at least one circuit is further configured to delete the identification information recorded in the memory when a predetermined period of time has passed after a power-supply of the controller has been turned off.

5. The controller according to claim 1, wherein the at least one circuit is further configured to control recording, in a memory provided in the endoscope, a fact that the inspection operation has been performed, and determine, based on information recorded in the memory, whether or not the inspection operation has been performed for the endoscope when the self-propelled mechanism of the endoscope has been connected to the controller.

6. The controller according to claim 5, wherein the at least one circuit is further configured to
record, in the memory provided in the endoscope, information on a time:
when the self-propelled mechanism of the endoscope is connected to the controller; and
after the inspection operation has been performed, and
determine, based on the information on the time recorded in the memory, that the inspection operation has not been performed for the endoscope when a first predetermined period of time has passed after the self-propelled mechanism of the endoscope has been detached from the controller, or when a second predetermined period of time has passed after a power-supply of the controller has been turned off.

7. An insertion apparatus comprising:
the controller according to claim 1, and
the endoscope.

8. The insertion apparatus according to claim 7, wherein the self-propelled mechanism comprises: a rotating cylindrical body provided on an outer circumferential face of the insertion section, so as to be rotatable around a longitudinal axis of the insertion section; a motor that rotates the rotating cylindrical body; and the projection comprises a fin which is formed in the spiral shape on an outer circumferential face of the rotating cylindrical body, and which inserts or removes the insertion section in accordance with the rotation of the rotating cylindrical body.

9. The controller according to claim 1, wherein the at least one circuit is further configured to permit the usual operation, upon determining that the self-propelled mechanism of the endoscope has been connected to the controller and the inspection operation has been performed for the endoscope.

10. The controller according to claim 1, wherein the at least one circuit is further configured to detect whether the self-propelled mechanism of the endoscope is connected to the controller.

* * * * *